US 6,531,288 B1

(12) United States Patent
Snutch et al.

(10) Patent No.: US 6,531,288 B1
(45) Date of Patent: Mar. 11, 2003

(54) METHODS TO IDENTIFY COMPOUNDS THAT AFFECT THE EXPRESSION LEVEL OF THE SYNTAXIN-1 A ENCODING GENE

(75) Inventors: Terrance P. Snutch, Vancouver (CA); John McRory, N. Vancouver (CA); Kathy G. Sutton, Herts (GB)

(73) Assignee: University of British Columbia, Vancouver (CA)

( * ) Notice: Subject to any disclaimer, the term of this patent is extended or adjusted under 35 U.S.C. 154(b) by 0 days.

(21) Appl. No.: 09/688,295

(22) Filed: Oct. 13, 2000

Related U.S. Application Data

(60) Provisional application No. 60/159,095, filed on Oct. 13, 1999.

(51) Int. Cl.[7] ............................ G01N 33/53; C12Q 1/68
(52) U.S. Cl. ............................. 435/7.1; 435/6; 436/501
(58) Field of Search .................... 435/7.1, 69.1, 435/6; 530/325; 436/501

(56) References Cited

U.S. PATENT DOCUMENTS

| | | | |
|---|---|---|---|
| 5,623,051 A | 4/1997 | Catterall et al. | 530/324 |
| 6,090,631 A | 7/2000 | Catterall et al. | 436/501 |

FOREIGN PATENT DOCUMENTS

| | | | |
|---|---|---|---|
| JP | 09 299092 A | 11/1997 | |
| WO | WO 95/04822 A | 2/1995 | |
| WO | WO 96/15149 A | 5/1996 | |

OTHER PUBLICATIONS

Sutton et al. P/Q–type calcium channels mediate the activity–dependent feedback of syntaxin–1A. Nature, 401:800–804, 1999.*

Xiao et al., (1998) *Neuron* 21:707–716.

Zhuchenko,O. et al. (1997). *Nature Genetics* 15:62–69.

Tu et al., "Homer Binds a Novel Proline–Rich Motif and Links Group 1 Metabotropic Glutamate Receptors with IP3 Receptors," Neuron (1998) 21:717–726.

Xiao et al., "Homer: a Link Between Neural Activity and Glutamate Receptor Function," Current Opinion in Neurobiology (2000) 10:370–374.

\* cited by examiner

*Primary Examiner*—Elizabeth Kemmerer
*Assistant Examiner*—Ruixiang Li
(74) *Attorney, Agent, or Firm*—Morrison & Foerster LLP

(57) ABSTRACT

A specific amino acid sequence proximal to the carboxy terminus of P/Q type ion channels has been shown to mediate, through binding to the Homer protein, the expression of the gene encoding syntaxin-1A. This region of the P/Q type calcium ion channel provides peptides that can be used in screening assays for compounds that modulate the central nervous system.

9 Claims, No Drawings

METHODS TO IDENTIFY COMPOUNDS THAT AFFECT THE EXPRESSION LEVEL OF THE SYNTAXIN-1 A ENCODING GENE

Cross-Reference to Related Applications

This application claims priority under 35 U.S.C. §119(e) from provisional application No. 60/159,095 filed Oct. 13, 1999, the contents of which are incorporated herein by reference.

TECHNICAL FIELD

The invention relates to the field of neural transmission and drug discovery.

BACKGROUND ART

U.S. Pat. Nos. 6,090,631 and 5,623,051, incorporated herein by reference, describe a region of the P/Q and N-type calcium ion channels which binds syntaxin and SNAP-25 proteins. This region is located between domains II and III of the $\alpha_1$ subunit of these channels. Syntaxin and SNAP-25 are proteins which mediate the docking of presynaptic vesicles required for release of neurotransmitters. As described in these documents, these syntaxin/SNAP-25 binding regions can be used to screen for compounds that will block the binding of these regions to syntaxin and/or SNAP-25, thus inhibiting neuronal transmission.

The conditions surrounding the transmission of signals through neuronal networks clearly affects a variety of physiological responses, including perception of pain, learning, memory, and the like. Modulation of the level of neural transmission and the condition of the presynaptic environment have profound physiological effects, primarily within the nervous system. The primary calcium ion channels that effect neural transmission are these N and P/Q type channels. P/Q type channels have been implicated mostly in the presynaptic terminals of the central nervous system (CNS) while the N type channels appear to dominate in the peripheral nervous system. Thus, P/Q type channels are particularly important in CNS functions such as memory and pain.

Calcium ion channels in general are composed of $\alpha_1$ subunits which $\alpha_1$ subunits are optionally coupled with additional subunits, but can function alone. According to current terminology, N type channels are comprised of $\alpha_{1B}$ subunits while P/Q channels are composed of $\alpha_{1A}$ subunits.

It would clearly be desirable to provide compounds that are able to control the presynaptic environment so as to permit a greater control over central nervous system functions, including memory, learning and pain. The present invention provides a mechanism for this control. As will be shown below, a specific region of the $\alpha_{1A}$ subunit contains a sequence which binds to the known protein Homer which is described in articles by Xiao, B., et al., Cur. Opinion in Neurobiol. (2000) 10:370–374 and by Tu, J. C., et al., Neuron (1998) 21:717–726. The disclosures of these articles are incorporated herein by reference. As shown in these articles, the Homer protein binds to a multiplicity of targets which are important in signaling and neurotransmission. A consensus sequence which is proline rich is also described.

DISCLOSURE OF THE INVENTION

The invention resides in the identification of a peptide region specific to the P/Q calcium ion channel that is responsible for the cascade of events that results in expression of the gene encoding syntaxin-1A. Thus, use of this peptide in screening assays permits identification of compounds that can be used to regulate the levels of syntaxin-1A available in the presynaptic region and thus modulate such functions as learning, memory and pain.

According to the discovery of the applicants herein, calcium flow through the P/Q ion channel specifically effects the expression of the gene encoding syntaxin in model cell systems and in neuronal cells per se. It has now been found that a specific 4-amino acid sequence approximately 200 amino acids from the C terminus of the P/Q calcium ion channel is the site for interaction of this channel with Homer, a protein known to affect intracellular calcium ion stores, and this interaction is essential for the ability of the P/Q calcium ion channel to effect the expression of the syntaxin-1A encoding gene.

Thus, in one aspect, the invention is directed to a method to identify compounds that affect central nervous system function, such as learning and memory, which method comprises contacting a candidate compound with a peptide that comprises the binding site for Homer which resides proximal to the carboxy terminus of the P/Q calcium ion channel and determining whether said compound binds to said peptide. Compounds that bind to this peptide are identified as compounds that affect central nervous system (CNS) function. This screening assay can be conducted in a straightforward manner by simply assessing the ability of the compound to bind. More commonly, the ability of the candidate compound to inhibit the binding of a ligand known to bind the peptide, including the ability of Homer to so bind, can be used to assess said binding.

In another aspect, the invention is directed to a peptide comprising the sequence of the binding site flanked by additional amino acids, typically those which flank the binding site in the native ion channel, and to antibiotics that are immunospecific for this region. In other aspects, the invention is directed to the compounds so identified and to methods to modulate CNS function using these compounds.

MODES OF CARRYING OUT THE INVENTION

The present applicants have shown that calcium influx selectively through P/Q type calcium ion channels is responsible for activating expression of syntaxin-1A, a presynaptic protein that plays a central role in mediating vesicle docking, fusion and neurotransmitter release. Applicants have demonstrated that the initial calcium ion signal is amplified through calcium ion from intracellular stores and acts via phosphorylation that is dependent on a number of cofactors including CaMK II/IV, PKA, and MAPKK. As syntaxin-1A interacts with P/Q type calcium ion channels to decrease channel availability, the expression of the gene encoding syntaxin-1A is regulated by an activity-dependent feedback pathway.

Applicants have now shown that the interaction of the initial extracellular calcium signal with the calcium released from intracellular stores is mediated by binding of the known protein Homer to a specific amino acid sequence proximal to the C terminus of the P/Q type ion channel and is specific for the P/Q $\alpha_{1A}$ subunit as opposed to other known calcium ion channels. Identification of this binding site permits the use of peptides containing this site as screening tools for important compounds which modulate CNS activity.

Methods for conducting such screening assays are well known in the art. Typically, the target peptide is produced recombinantly in suitable host cells and displayed at the surface of said host cells or is coupled to a solid support. Such coupling may be covalent coupling or may be achieved through non-covalent adsorption, such as, for example, by providing a histidine tag and associating the resulting fusion protein to a solid support through a metal chelate. A wide variety of methods for providing an assayable form of the peptide is known in the art. Indeed, as the required peptide is relatively short, direct synthesis on a solid support is one convenient way of providing this peptide.

The specific site required for binding is the four amino acid sequence PLMF. In order to render the assay practical and specific, however, it is desirable to include additional amino acid sequence at one or both of the N and C terminus of this tetrapeptide. Preferred embodiments for such additional amino acid sequence are the sequences present in the native ion channels. Typically, sequences extending 20 amino acids upstream and/or downstream, more preferably 15 amino acids upstream and/or downstream, or even 10 or 5 or 2 amino acids of the sequences upstream and/or downstream of the required tetrapeptide are employed.

The sequence containing the tetrapeptide with the tetrapeptide itself in bolded and underlined types is as follows:

1966-YYRQSKAKKL QAMREEQDRT PLMFQRMEPP SPTQEGGPGQ NALP-2009 (SEQ ID NO:1).

This sequence is derived from one allele encoding a human P/Q type calcium channel. It is understood that similar sequences are included in the corresponding P/Q channels of other mammalian species, and peptides derived from these species as well as from allelic variants of the sequence shown above may be used in the method of the invention. In general, it is preferred to utilize peptides containing sequence derived from the above-shown sequence which are at least 90% homologous, preferably 95% homologous, more preferably 97% homologous and more preferably 99% homologous with the sequence shown above, or a fragment thereof as long the required tetrapeptide is included.

Methods for conducting the assay once the peptide is made available, preferably displayed on cells or on a solid support, are well known in the art. As noted above, compounds can be assessed for binding directly by providing them with labels, or, for example, using homogenous assays wherein the peptide itself is labeled and the detectability of signal ascribed to the label is affected by the peptide being in a bound or unbound state. Alternatively, and perhaps more conveniently, the binding may be assessed by ability of the compound to inhibit the binding of a ligand known to bind to the P/Q peptide, and to the tetrapeptide essential portion thereof specifically. Such "ligands" would include antibodies specific to this epitope, including antibodies in the various forms, such as single-chain Fv regions, Fab fragments, etc., the Homer protein which is the native ligand, or, indeed, any compound which has previously been determined to bind to this site. A wide variety of detection methods for such inhibition of known ligand binding is known. Typically, the competing known ligand is labeled and a decrease in label bound to the solid support (if the peptide is thus supported) provides an assessment of such inhibition. Labels may include fluorescent labels, chromogenic labels, enzyme labels, radioisotope labels, and the like. Again, homogenous assays may be convenient. For example, fluorescence quenching assays wherein both the peptide and the competing ligand contain label are known. The invention resides in the nature of the peptide used as the target, not in the specific design of the screening assay.

Compounds that are identified in this screen will clearly influence the status of signaling in the neuronal pathway of a subject administered these compounds. The subject may be a laboratory animal used to study patterns of learning and memory, such as rats, mice and rabbits. The subject may also be a human subject where it is desired to alter a deficit in memory or assuage some other physiological disorder. Administration of such compounds to subjects is by standard procedures and uses formulations such as those in *Remington's Pharmaceutical Sciences*, latest edition, Mack Publishing Co., Easton, Pa., incorporated herein by reference. Thus, the compounds identified using the method of the invention could, for example, be administered to murine models of specific CNS based or other neurological based conditions and the effect of such compounds on the model will elucidate the mechanisms associated with the condition.

The applicants herein have verified the nature of the elevation of expression of syntaxin-1A through calcium ion transit of the ion channel P/Q as follows:

First, it was shown that transient expression of human $\alpha_{1A}$ (P/Q type) calcium channels in HEK293 cells resulted in a negative steady state inactivation which, in turn, suggested a corresponding interaction with syntaxin. This was confirmed by incubation with botulism toxin C1 which shifted the steady state inactivation, but did not affect the voltage dependence of current activation. In addition, these results were affected as expected by the presence of an antisense syntaxin construct.

It was further shown that syntaxin-1A was not endogenously expressed in HEK293 cells while the presence of the syntaxin-1A protein was detected in HEK293 cells transfected with the $\alpha_{1A}$ P/Q type calcium channel; mRNA corresponding to syntaxin-1A was also detected, but inhibited when the cells were incubated in actinomycin D. Syntaxin-1A was the only SNARE protein produced in these cells; syntaxin 1B, SNAP-25, synaptophysin, VAMP, and synaptotagmin were not detected.

There was no evidence for production of syntaxin-1A in HEK293 cells transfected with calcium ion channel $\alpha_2\delta$ or $\beta_{1B}$ subunits. Cells transfected with $\alpha_{1B}$ (N type); $\alpha_{1C}$ (L type); $\alpha_{1E}$ (novel type); and the $\alpha_{1G}$ and $\alpha_{11}$ T type channels also failed to result in production of syntaxin-1A mRNA. The possibility that the specificity of P/Q type channels in inducing syntaxin-1A production was eliminated using appropriate controls.

In the presence of various selected P/Q type channel antagonists, production of syntaxin-1A, mRNA or protein was undetectable.

It was confirmed that the presence of the P/Q type channels in transfected HEK293 cells resulted in an enhanced intracellular calcium ion concentration. It appears to be this intracellular enhanced calcium ion concentration which results in syntaxin-1A production since ionomycin at concentrations of 10 nM-2 μM, which non-specifically enhances intracellular calcium ion concentration, defined a discrete upper and lower limit of intracellular calcium ion dependent activation with maximal activation occurring at levels of 50–200 nM.

Having established that expression of the syntaxin-1A gene is specifically induced by calcium flux mediated by P/Q ion channels, applicants elucidated the subsequent transduction pathway using agents that alter intracellular calcium concentration. Application of thapsigargin stimulated syntaxin-1A expression in untransfected cells, and, in $\alpha_{1A}$ transfected cells both BAPTA-AM and EGTA-AM blocked the calcium dependent induction of syntaxin-1A. Either caffeine or carbachol activated calcium release from ryanodine —and $IP_3$—sensitive stores rapidly and stimulated syntaxin-1A mRNA levels in untransfected cells. This was inhibited using agents which block release from either of these stores. In general, the foregoing data suggest that a discrete level of basil $\alpha_{1A}$ specific calcium influx induces syntaxin-1A expression through a secondary calcium release from intracellular stores. Syntaxin-1A expression in $\alpha_{1A}$ transfected cells could be inhibited with compounds known to block tyrosine kinase, calmodulin activity or CaMK II/IV or PKA activities. Activators of PKA induced syntaxin MRNA even in the absence of $\alpha_{1A}$ transfection. Activation of protein kinase C did not induce expression. A portion of the transduction pathway may also involve the transcription factor CREB, as it was determined that the level of phosphorylated CREB is up-regulated in the transfected HEK cells.

The foregoing results in HEK293 transfected cells were correlated with the endogenous P/Q type channels in neurons. Syntaxin-1A is basally expressed in cerebellar granule cells, but this is inhibited by ω Agatoxin IVA, which is known to inhibit calcium P/Q type channels specifically. Inhibitors of N or L type channels did not block calcium dependent expression of syntaxin-1A. Treatment of these cerebellar granule cells, which had been incubated in ω Agatoxin IVA with thapsigargin recovered the syntaxin-1A expression.

Syntaxin-1A expression was inhibited by the same agents as had inhibited it in HEK293 cells including inhibitors of ryanodine —or $IP_3$—induced calcium release from stores, of CaM kinase II/IV, and of PKA, or MAPKK.

In summary, P/Q type selective calcium influx induces expression of syntaxin-1A but not of other SNARE proteins involved in vesicle fusion and neurotransmitter release. It appears to be under tight spatial and temporal calcium dependent control and is apparently mediated by an association with intracellular calcium stores.

Further, applicants have identified the initial critical step in the transduction pathway which is the binding of the Homer protein to a specific site in the $\alpha_{1A}$ channel subunit proximal to the C terminus. The availability of a peptide containing this site permits the identification of compounds that are useful in elucidating neuronal pathways, and in modulating the CNS in subjects in general, including treating disorders of the CNS especially those involving learning and memory.

---

---

What is claimed is:

1. A method to identify compounds that affect the expression level of the syntaxin-1A encoding gene which method comprises contacting a candidate compound with a peptide that consists essentially of the binding site for Homer proximate to the carboxy terminus of the P/Q calcium ion channel; and determining whether said compound binds to said peptide;

wherein a candidate compound which binds to said peptide is identified as a compound that affects the expression level of the syntaxin-1A encoding gene.

2. The method of claim 1 wherein said contacting is in the presence of a ligand known to bind said peptide, and said determining comprises assessing the ability of said candidate compound to displace said ligand.

3. The method of claim 1 wherein the peptide comprises the amino acid sequence PLMF (amino acid residues 21–24 of SEQ ID NO:1).

4. The method of claim 3 wherein the PLMF sequence (amino acid residues 21–24 of SEQ ID NO:1) is flanked by 10 amino acids upstream and/or downstream of the sequence PLMF (amino acid residues 21–24 of SEQ ID NO:1) in said P/Q ion channel.

5. The method of claim 1 wherein the peptide contains 44 amino acids, comprises PLMF (amino acid residues 21–24 of SEQ ID NO:1), and is at least 95% homologous to the sequence 1966-YYRQSKAKKLQAMREEQDRT PLMFQRMEPP SPTQEGGPGQ NALP-2009 (SEQ ID NO:1) over its entire length or comprises PLMF (amino acid residues 21–24 of SEQ ID NO:1) and is a fragment of said 44 amino acid peptide.

6. The method of claim 1 wherein the peptide is provided as cells which comprises an expression system for a compound comprising the sequence PLMF (amino acid residues 21–24 of SEQ ID NO:1) which expression system comprises a nucleotide sequence encoding said peptide operably linked to sequences that affect expression.

7. The method of claim 5, wherein the peptide has the sequence 1966-YYRQSKAKKLQAMREEQDRT PLMFQRMEPPSPTQEGGPGQ NALP-2009 (SEQ ID NO:1) or comprises PLMF (amino acid residues 21–24 of SEQ ID NO:1) and is fragment of said sequence.

8. The method of claim 1, wherein the peptide has the sequence QAMREEQDRTPLMFQRMEPPSPTQ (amino acid residues 11 to 34 of SEQ ID NO:1).

9. The method of claim 1, wherein the peptide has the sequence REEQDRTPLMFQRMEPP (amino acid residues 14–30 of SEQ ID NO:1).

* * * * *

SEQUENCE LISTING

<160> NUMBER OF SEQ ID NOS: 1

<210> SEQ ID NO 1
<211> LENGTH: 44
<212> TYPE: PRT
<213> ORGANISM: Homo sapiens

<400> SEQUENCE: 1

```
Tyr Tyr Arg Gln Ser Lys Ala Lys Lys Leu Gln Ala Met Arg Glu Glu
 1               5                  10                  15

Gln Asp Arg Thr Pro Leu Met Phe Gln Arg Met Glu Pro Pro Ser Pro
            20                  25                  30

Thr Gln Glu Gly Gly Pro Gly Gln Asn Ala Leu Pro
        35                  40
```